United States Patent
Choi et al.

(10) Patent No.: US 11,464,598 B2
(45) Date of Patent: Oct. 11, 2022

(54) ORAL FIXATION DEVICE AND METHOD FOR RADIATION THERAPY OF LIP CANCER

(71) Applicant: UNIVERSITY OF ULSAN FOUNDATION FOR INDUSTRY COOPERATION, Ulsan (KR)

(72) Inventors: Won Sik Choi, Gangneung-si (KR); Woo Sang Ahn, Gangneung-si (KR); Seong Soo Shin, Gangneung-si (KR); Woo Suk Lee, Gangneung-si (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 357 days.

(21) Appl. No.: 16/746,818

(22) Filed: Jan. 18, 2020

(65) Prior Publication Data

US 2020/0222722 A1    Jul. 16, 2020
US 2020/0360725 A9    Nov. 19, 2020

Related U.S. Application Data

(63) Continuation of application No. PCT/KR2018/009647, filed on Aug. 22, 2018.

(30) Foreign Application Priority Data

Jul. 20, 2017  (KR) .................. 10-2017-0092283

(51) Int. Cl.
*A61B 90/16*     (2016.01)
*A61N 5/10*     (2006.01)
(Continued)

(52) U.S. Cl.
CPC ................ *A61B 90/16* (2016.02); *A61B 1/24* (2013.01); *A61B 6/145* (2013.01); *A61N 5/1049* (2013.01);
(Continued)

(58) Field of Classification Search
CPC .... A61B 1/24; A61B 6/04; A61B 6/10; A61B 6/107; A61B 6/14; A61B 6/145;
(Continued)

(56) References Cited

U.S. PATENT DOCUMENTS 4,223,229 A *  9/1980  Persico ..................... G21F 3/02
                                         976/DIG. 336
5,590,643 A *  1/1997  Flam .................. A61M 16/0488
                                         128/207.14
(Continued)

FOREIGN PATENT DOCUMENTS

JP    2005-058594 A    3/2005
JP    2016-032595 A    3/2016
(Continued)

OTHER PUBLICATIONS

International Search Report issued in PCT/KR2018/009647; dated Jan. 2, 2019.

*Primary Examiner* — Anastasia Midkiff
(74) *Attorney, Agent, or Firm* — Studebaker & Brackett PC

(57) ABSTRACT

Disclosed are an oral fixation device for radiation therapy and an oral fixation method in treatment of a lip cancer. The oral fixation device for radiation therapy includes a first spacer including a first insert inserted between a first lip portion and a first gum portion, and a tooth support coupled to the first spacer at a side of the first spacer disposed inwardly of an oral cavity, wherein teeth or gums of a patient is supported on the tooth support, wherein a first spacer has a specific thickness to maintain a specific spacing between the first lip portion and the first gum portion, wherein the first lip portion includes a treatment target portion to be subjected to the radiation therapy.

9 Claims, 13 Drawing Sheets

(51) Int. Cl.
*A61B 1/24* (2006.01)
*A61B 6/14* (2006.01)
*A61B 90/00* (2016.01)

(52) U.S. Cl.
CPC ....... *A61B 2090/036* (2016.02); *A61N 5/1014* (2013.01); *A61N 2005/1094* (2013.01); *A61N 2005/1097* (2013.01)

(58) Field of Classification Search
CPC ......... A61B 17/24; A61B 90/02; A61B 90/03; A61B 90/04; A61B 90/08; A61B 90/10; A61B 90/14; A61B 90/16; A61B 2090/033; A61B 2090/034; A61B 2090/036; A61B 2090/0409; A61B 2090/0436; A61B 2090/0481; A61B 2560/02; A61B 2560/04; A61B 2560/0406; A61N 5/10; A61N 5/1048; A61N 5/1049; A61N 2005/1063; A61N 2005/1092; A61N 2005/1094; A61N 2005/1097; A61C 19/06; A61D 5/00; A61D 15/00; A61K 6/00
See application file for complete search history.

(56) References Cited

U.S. PATENT DOCUMENTS

| | | | |
|---|---|---|---|
| 2005/0196725 | A1* | 9/2005 | Fu ...................... A61C 17/0211 433/216 |
| 2010/0292526 | A1* | 11/2010 | Schuman .............. B29C 64/135 600/3 |
| 2019/0239978 | A1* | 8/2019 | Holman ................ A61C 9/0006 |
| 2019/0357992 | A1* | 11/2019 | Calhoun .................. A61C 9/00 |
| 2019/0366122 | A1* | 12/2019 | Holman ................ A61B 90/16 |

FOREIGN PATENT DOCUMENTS

| | | |
|---|---|---|
| KR | 10-2013-0128805 A | 11/2013 |
| KR | 101478118 B1 | 12/2014 |
| KR | 10-1668178 B1 | 10/2016 |
| KR | 10-2017-0049238 A | 5/2017 |

* cited by examiner

ORAL FIXATION DEVICE AND METHOD FOR RADIATION THERAPY OF LIP CANCER

CROSS-REFERENCE TO RELATED APPLICATIONS

The present application is a continuation of International Patent Application No. PCT/KR2018/009647, filed on Aug. 22, 2018 which is based upon and claims the benefit of priority to Korean Patent Application No. 10-2017-0092283 filed on Jul. 20, 2017. The disclosures of the above-listed applications are hereby incorporated by reference herein in their entirety.

BACKGROUND

Embodiments of the inventive concept described herein relate to an oral fixation device for radiation therapy and an oral fixation method in treatment of a lip cancer. More specifically, embodiments of the inventive concept described herein relate to an oral fixation device and an oral fixation method used in radiation therapy of a patient with a lip cancer.

Radiation therapy involves use of radiation to treat diseases and is one of three major therapies for tumor therapy along with surgery and chemotherapy.

A therapeutic radiation among radiations used for medical purposes is applied to a tumor of a cancer patient so that cancer cells may no longer reproduce to kill the cancer cells at an end of life thereof or to relieve a pain.

Such radiation therapy is used to prevent recurrence of a cancer when cancer cells are more likely to remain after surgery, or is used when surgery is not possible, or is used when radiation therapy is more effective than surgery, or is used to improve a quality of life of a patient by combining surgery and radiation therapy, or is used in a combination manner with chemotherapy to maximize an anticancer effect after the chemotherapy.

SUMMARY

When a lip cancer (carcinoma of a lip) is treated with radiation, the radiation is applied to gums adjacent to a lip or a lip portion (e.g., a lower lip which is in a normal state when a tumor occurs in an upper lip) rather than a lip portion having a tumor to cause damage thereto. Therefore, there is a need for an assistive device to allow a tumor-free normal body part (particularly, an opposite lip or gums) not to be affected by the radiation or a device for fixing a lip having the lip cancer.

Embodiments of the inventive concept provide an oral fixation device for radiation therapy and an oral fixation method in lip cancer treatment by which gums adjacent to a lip portion having a cancer tumor or a normal opposite lip portion thereto is spaced from the lip portion having the cancer tumor such that a normal tissue is not damaged by radiation.

Purposes to be achieved by the inventive concept are not limited to those as mentioned above. Still other purposes as not mentioned will be clearly understood by those skilled in the art from following descriptions.

According to an exemplary embodiment, an oral fixation device for radiation therapy may include a first spacer including a first insert inserted between a first lip portion and a first gum portion, and a tooth support coupled to the first spacer at a side of the first spacer disposed inwardly of an oral cavity, wherein teeth or gums of a patient is supported on the tooth support, wherein the first spacer has a specific thickness to maintain a specific spacing between the first lip portion and the first gum portion, wherein the first lip portion includes a treatment target portion to be subjected to the radiation therapy.

Further, in one embodiment, the first spacer may further include a second insert disposed between a second lip portion and a second gum portion, wherein the second insert may have a specific height to maintain a spacing between the first lip portion and the second lip portion at a spacing equal to or larger than a first spacing.

Further, in another embodiment, the oral fixation device may further include a target support protruding from the first spacer toward the first lip portion, wherein the target support may be disposed between the first lip portion and the first gum portion to maintain a specific second spacing between the first lip portion and the second gum portion.

Further, in another embodiment, the target support may have a curvature conforming to a front mouth shape when a mouth is open.

Further, in another embodiment, the oral fixation device may further include a target support protruding from the first spacer toward the first lip portion, wherein the target support may be formed to allow the treatment target portion to be placed at a constant position during a plurality of times of radiation therapy.

Further, in another embodiment, the oral fixation device may further include a radiation shield received inside the first spacer.

Further, in another embodiment, the oral fixation device may further include a handle coupled to the first spacer or the tooth support, wherein the handle extends out of the oral cavity.

Further, in another embodiment, the tooth support may have a plurality of teeth receiving grooves having different spacings from the first spacer.

Further, in another embodiment, the oral fixation device may further include one or more air communication holes defined in the second insert, wherein air may be introduced through the air communication holes into the oral cavity for breathing.

According to an exemplary embodiment, a method of fixing an oral cavity in treatment of a lip cancer using the oral fixation device may include inserting the oral fixation device into the oral cavity such that the first insert of the first spacer is placed on the first lip portion having the treatment target portion; and placing the teeth or the gums of the patient on the tooth support of the oral fixation device.

According to the inventive concept as described above, following various effects may be achieved.

First, the lip portion in which the tumor is located may be spaced apart from another normal body portion, thereby preventing the normal tissue from being damaged upon irradiation toward the tumor tissue.

Second, the optimal oral fixation device may be selected and used based on a type of the radiation device as used (i.e., the electron beam application device or the photon beam application device). For example, when performing the lip cancer treatment using the photon beam, the photon beam may be irradiated toward the tumor from a side of the lip. Thus, the oral fixation device may be used to maintain a specific spacing between the lip and the gum so that the photon beam is not irradiated to the normal gum tissue.

Third, when the radiation therapy is performed multiple times, the patient's teeth or gums tip may be placed in the same teeth receiving grooves of the tooth support. Thus, the radiation therapy may be repeated by reproducing the same oral cavity fixation state. In this way, the radiation treatment may be simply and repeatedly performed on the same lesion, that is, the tumor location.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
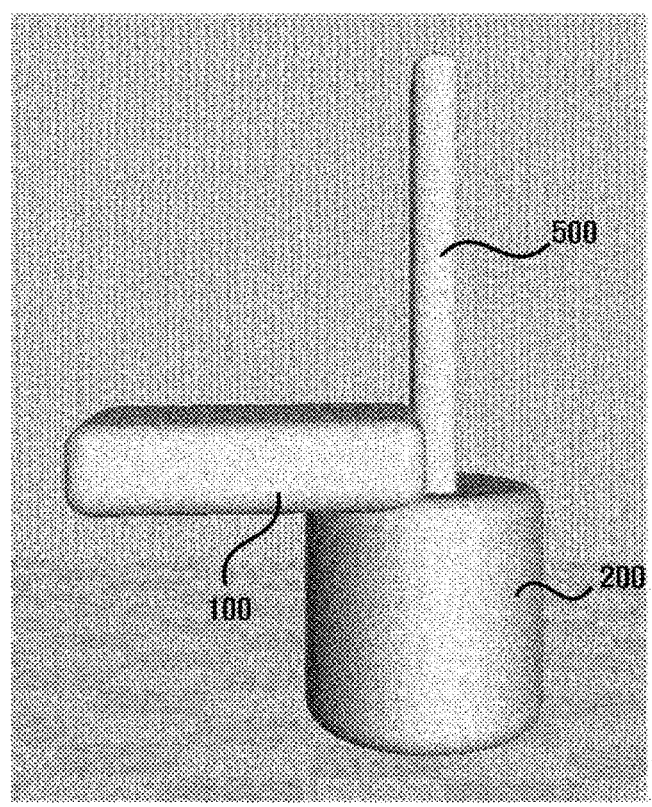
FIG. 1 shows an example of an oral fixation device according to an embodiment of the inventive concept.

Hereinafter, exemplary embodiments of the inventive concept will be described in detail with reference to the accompanying drawings. Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to merely fully inform those skilled in the art of the inventive concept of the scope of the inventive concept. The inventive concept is only defined by the scope of the claims. Like reference numerals refer to like elements throughout the disclosure.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Hereinafter, an oral fixation device for radiation therapy and an oral fixation method for lip cancer treatment according to embodiments of the inventive concept will be described in detail with reference to the accompanying drawings.

FIG. 1 shows an example of an oral fixation device for radiation therapy according to an embodiment of the inventive concept.

Referring to FIG. 1, the oral fixation device for radiation therapy according to an embodiment of the inventive concept includes a first spacer 100, and a tooth support 200.

The first spacer 100 serves to maintain a specific spacing between a lip where a tumor is located and gums adjacent thereto. The first spacer 100 may be formed to have a specific thickness to maintain a specific spacing between a first lip portion and a first gum portion.

In one embodiment, the first spacer 100 includes a first insert 110 inserted between the first lip portion and the first gum portion. The first lip portion means a specific lip where a tumor as a treatment target portion to be subjected to radiation therapy is located. The first gum portion is gums adjacent to the first lip portion, that is, in contact with the first lip portion. The first insert is placed between the first lip portion and the first gum portion to space the first gum from the first lip portion such that the first gum is not subjected to the radiation.

For example, when a photon beam are used as radiation, a radiation therapy device irradiates the photon beam from a side of a lip. Specifically, the photon beam has strong penetrating power. Thus, when the photon beam is irradiated from a front of the lip, an amount of radiation irradiated to gums increases. For this reason, the radiation therapy device irradiates the photon from a side of a lip such that the photon beam is irradiated toward a tumor area of the lip while not being directed to the gum. Although the radiation therapy device irradiates the photon from a side of the lip, the gum is affected by the photon beam when the lip and gum are located closed to each other. For this reason, the first insert 110 of the oral fixation device for radiation therapy is placed between the first lip portion where the tumor is located and the first gum portion to space the first gum portion and the first lip portion from each other.

Further, for example, an electron beam is used as the radiation. In this case, the electron beam has a weak penetrating power. Thus, when the electron beam is irradiated from a side of the lip, a transmission distance thereof is large and the beam does not reach a tumor region. For this reason, the radiation therapy device irradiates the electron beam from a front of the lip. In this case, although the electron beam has a weak penetrating power, the electron beam may penetrate the lip and then reach the gum. For this reason, the first insert 110 is placed between the first gum portion and the first lip portion to maintain the spacing therebetween so that the electron beam does not reach the gum. Further, as will be described later, as a shield is disposed in the first spacer 100, that is, the first insert 110, the electron beam may be completely prevented from reaching the gum.

Figure 2:
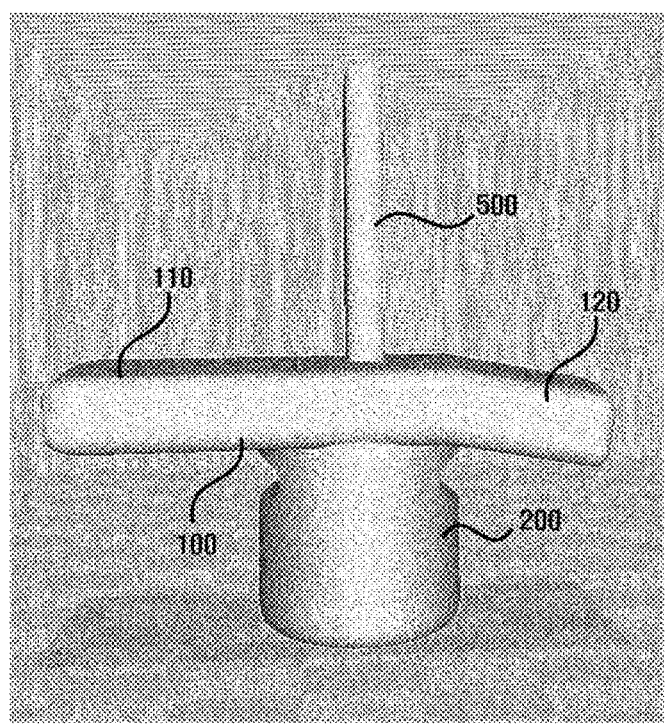
FIG. 2 shows an example of an oral fixation device in which a first spacer further includes a second insert according to an embodiment of the inventive concept.

In one embodiment, the first insert 110 may be formed to be oriented vertically while being located between the lip portion having the treatment target portion (i.e., the tumor) and the gum. In this way, when the radiation is irradiated from the front of the lip, the first lip portion where the tumor is located may be oriented to be perpendicular to a radiation irradiation direction. Further, when the oral fixation device further includes a handle 500 as described below, the first insert 110 and the handle 500 may be oriented vertically so that the handle 500 is not present in an irradiation range of the radiation Further, in another embodiment, as shown in FIG. 2, the first spacer 100 further includes a second insert 120. The second insert 120 may be disposed between a second lip portion and a second gum portion. As the first spacer 100 includes the first insert 110 and the second insert 120, the first spacer 100 may allow a vertical spacing between the first lip portion and the second lip portion to be equal to or larger than a certain spacing. That is, the first spacer 100 is constructed such that a spacing from a distal end of the first insert 110 to a distal end of the second insert 120 is a certain height, (i.e., a vertical spacing), thereby to maintain a spacing between the first lip portion and the second lip portion at a spacing equal to or larger than a first spacing.

The second lip portion has a normal tissue without a tumor. Thus, the second insert 120 may be formed such that the second insert 120 may be comfortably disposed between the second lip portion and the second gum portion while the second insert 120 does not have a specific thickness for separating the second lip portion and the second gum portion from each other by a specific spacing. For example, as shown in FIG. 2, the second insert 120 may be formed in an inclined shape corresponding to an inclination of the gum between the second lip portion and the second gum portion.

Further, as the second insert 120 is vertically connected to the first insert 110, the second insert 120 acts only to space the first lip portion and the second lip portion from each other by a spacing equal to or larger than a specific vertical spacing. Thus, a width in a front direction of the second insert 120 may be smaller than that of the first insert 110.

The tooth support 200 is coupled to the first spacer 100 at a side thereof as disposed inwardly of an oral cavity. The patient's teeth or gum is supported on the tooth support 200. In order to maintain a constant position of the oral fixation device during the radiation therapy, the tooth support 200 is bitten by the teeth or the gums (e.g., for a patient without the teeth) located at a top and a bottom of the patient's oral cavity. In this way, the oral fixation device may be inserted into the oral cavity and then a position thereof prior to a treatment start may be maintained during the radiation therapy. Thus, during the radiation therapy, the lip including the treatment target portion, that is, the tumor and a normal body portion may be prevented from being closer to each other by a spacing smaller than a specific spacing such that the normal body portion is prevented from being affected by the radiation.

Figure 3:
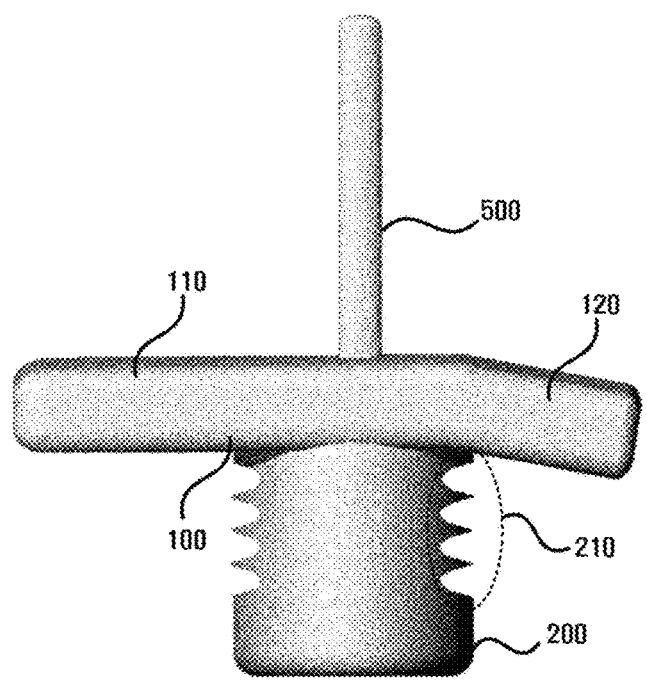
FIG. 3 shows an example of an oral fixation device having a plurality of teeth receiving grooves in accordance with an embodiment of the inventive concept.

Further, in another embodiment, the tooth support 200 has a plurality of teeth receiving grooves 210 having different spacings away from the first spacer 100. That is, as shown in FIG. 3, each of the plurality of teeth receiving grooves 210 may have a specific spacing from the first spacer 100. As the plurality of teeth receiving grooves 210 are formed in the tooth support 200, the patient may place the teeth or the gum into the teeth receiving grooves 210 having positions corresponding to an oral cavity structure thereof such that the radiation therapy may be executed in a comfortable state. Further, when the radiation therapy is performed periodically or several times, the patient may place the teeth or the gum into the same teeth receiving grooves 210, thereby to always bring out a constant oral cavity fixation state during the radiation therapy. In other words, reproducibility of the same treatment environment may be improved in a plurality of times of radiation therapy for the same patient.

Figure 4:
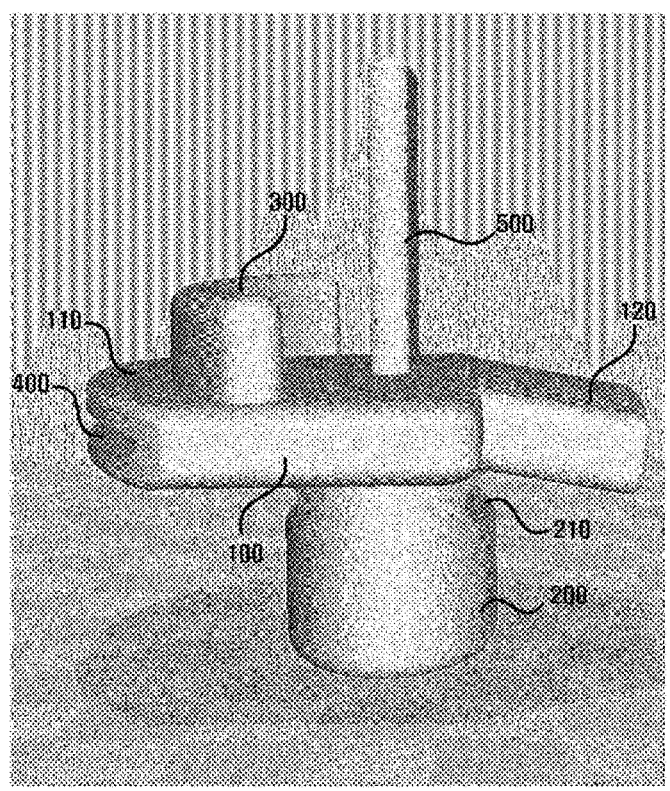
FIG. 4 shows an example of an oral fixation device further including a target support according to an embodiment of the inventive concept.

Further, in another embodiment, the oral fixation device further includes a target support 300. The target means a lip including a treatment target portion. As shown in FIG. 4, the target support 300 is formed to protrude from the first spacer 100 toward the first lip portion, and is disposed between the first lip portion and the first gum portion to maintain a specific second spacing between the first lip portion and the second gum portion. That is, as the target support 300 has a specific height, the target support 300 may increase a spacing between the first lip portion and the second lip portion to a sum of a thickness of the first spacer 100 and a maximum height of the target support 300 from a vertical level at which the target support 300 is coupled to the first spacer 100. That is, the second spacing between the first lip portion and the first gum portion may be a sum of the thickness of the first spacer 100 and the height of the target support 300 in the protruding direction. Therefore, as the target support 300 is formed, the thickness of the first spacer 100 may not increase to increase the spacing between the first lip portion and the second lip portion.

Figure 5:
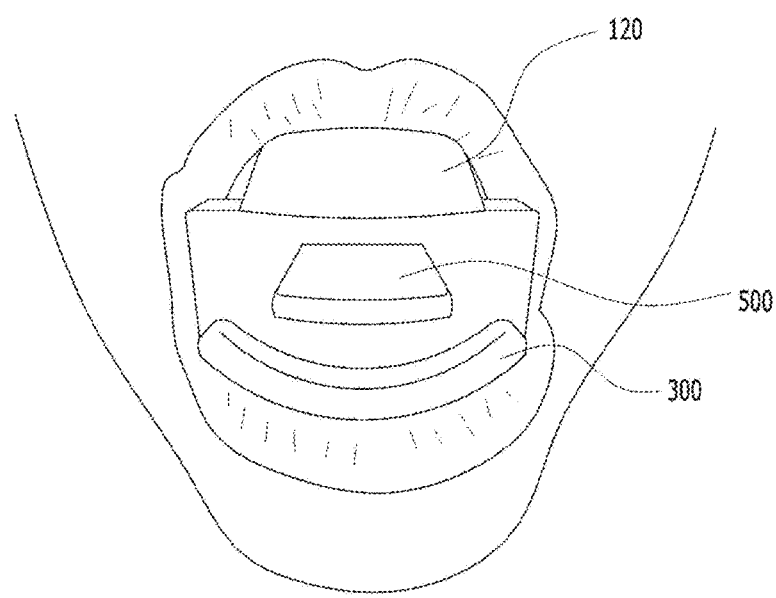
FIG. 5 shows a use example in which an oral fixation device is inserted into an oral cavity according to an embodiment of the inventive concept.

Further, in another embodiment, as shown in FIG. 4, the target support 300 may be formed to have a curvature corresponding to a front mouth shape when the mouth is opened. When a person opens a mouth, a circular mouth shape may be formed. Forming the target support 300 to have the curvature corresponding to the open mouth shape may result in an effect that when the oral fixation device is placed into the patient's oral cavity, as shown in FIG. 5, the target support 300 may be placed along a shape of the first lip portion to support the first lip portion.

Figure 9:
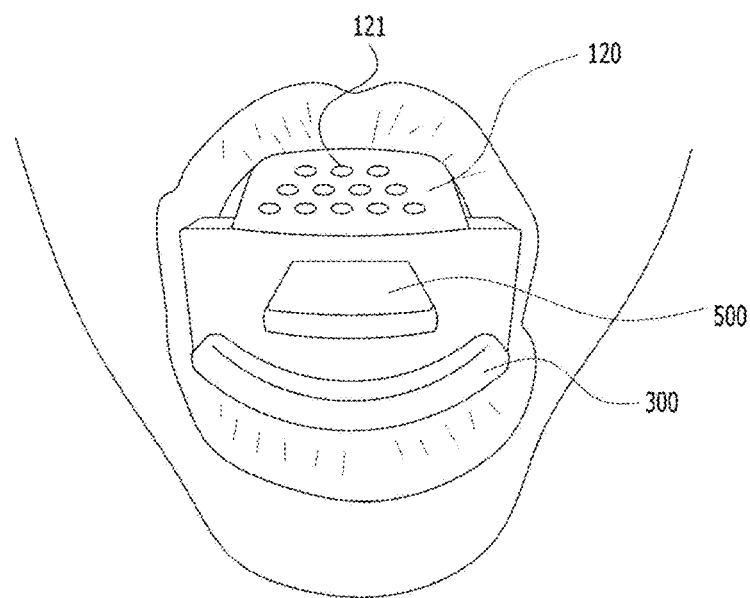
FIG. 9 shows an example in which a patient including a target portion wears an oral fixation device further including an air communication hole according to another embodiment of the inventive concept on a lower lip.

Further, in another embodiment, the target support 300 serves to fix a position of the lip to the same position during multiple times of radiation therapy. A lip portion as a radiation therapy target of a lip cancer patient is placed along a bottom surface or a front surface of the target support 300 as shown in FIG. 4 and FIG. 9. Thus, when the oral fixation device is placed while a placement position of the tooth support 200 is constant, the lip portion as the radiation therapy target is placed always at the same location. Therefore, this provides a high reproducibility at which a medical staff irradiates the radiation to the target in the same manner during a plurality of times of radiation therapy.

Figure 7A:
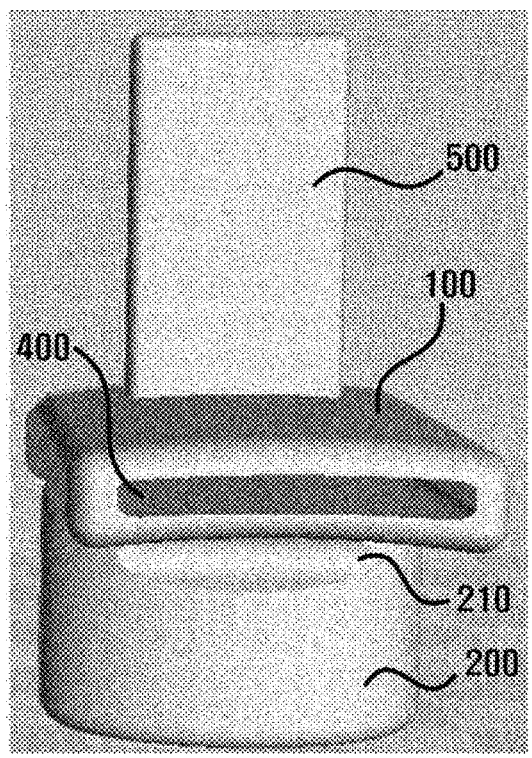
FIGS. 7A and 7B show examples of an oral fixation device having a space for receiving a radiation shield according to an embodiment of the inventive concept.
Figure 7B:
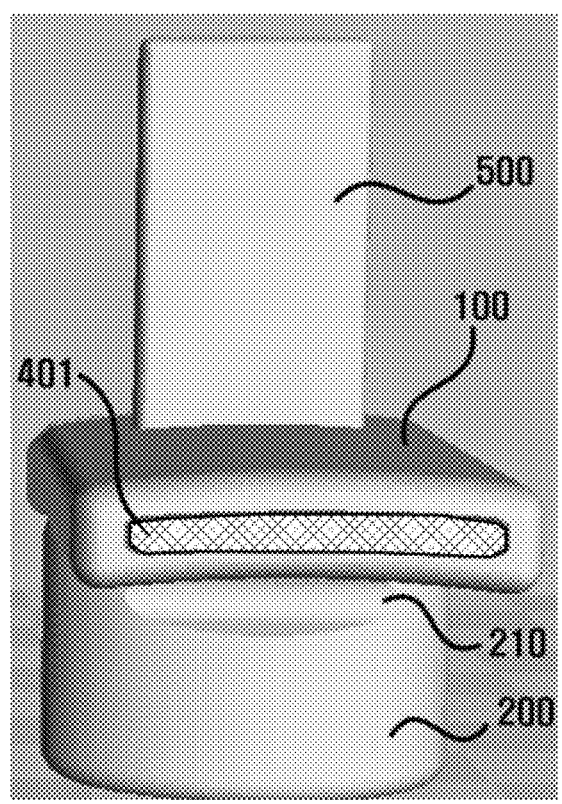

Further, in another embodiment, the oral fixation device further includes a radiation shield (401 in FIG. 7B). The radiation shield may be made of any material such as lead that may block radiation.

The radiation shield serves to prevent the radiation from reaching a body region behind the first spacer 100. That is, even though the first lip portion and the first gum portion are separated from each other by a specific spacing, the radiation shield may block the radiation.

Figure 6:
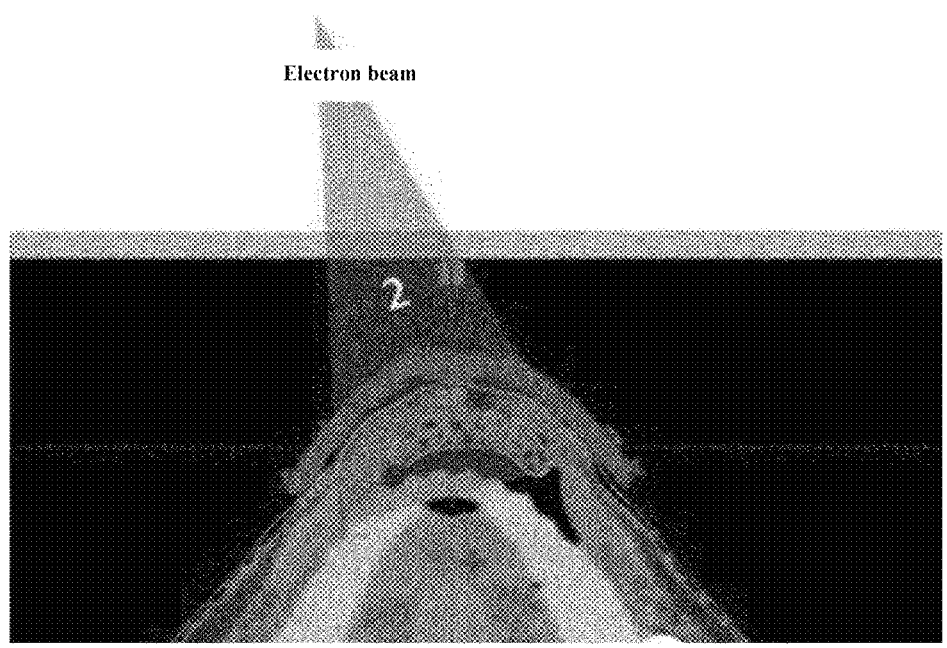
FIG. 6 shows an example of using an electron beam to treat a lip cancer.

Further, when the radiation is irradiated from a front of the lip, the radiation shield may prevent the radiation from entering the oral cavity. For example, as shown in FIG. 6, when the electron beam is irradiated from a front of the lip toward the oral cavity, some electron beams may propagate inside the oral cavity, thereby damaging a normal tissue inside the oral cavity. For this reason, the radiation shield is oriented in a vertical direction to block progression of the electron beam into the oral cavity.

In one embodiment, as shown in FIGS. 7A and 7B, the radiation shield 401 may be received inside the first spacer 100. That is, the radiation shield 401 may be received in a space formed inside the first spacer 100, that is, a shield receiving space 400. In another embodiment, the radiation shield 401 may be coupled to the first spacer 100 at a side thereof disposed inwardly of the oral cavity.

Further, in another embodiment, the oral fixation device further includes the handle 500. The handle 500 may be coupled to the first spacer 100 or the tooth support 200 so as to extend out of the oral cavity. As the oral fixation device is provided with the handle, a clinician may simply insert the oral fixation device into the patient's oral cavity and adjust the oral fixation device to an appropriate placement.

Further, in another embodiment, the first spacer 100 has one or more air communication holes defined therein. While the patient of the lip cancer is wearing the oral fixation device and is being subjected to radiation therapy, the oral cavity may be blocked, such that the patient has difficulty in breathing. In particular, the oral cavity of a patient who has difficulty in breathing through a nose may be blocked by the oral fixation device, such that he/she may have difficulty in breathing during radiation therapy. Thus, the oral fixation device may include one or more air communication holes passing through the first spacer 100.

Figure 8:
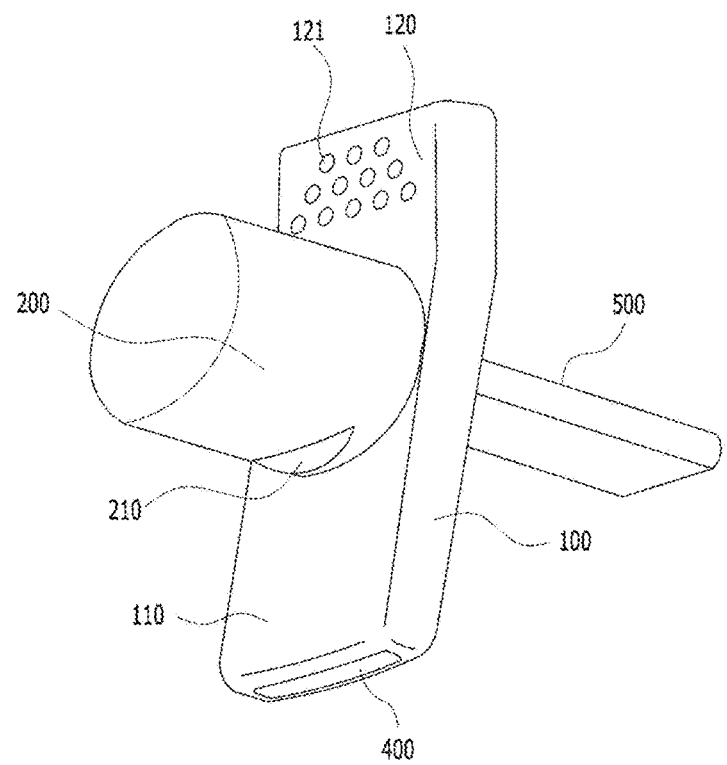
FIG. 8 shows an example of an oral fixation device further including an air communication hole according to another embodiment of the inventive concept.

In one embodiment, as shown in FIG. 8, at least one air communication hole 121 may be formed in the second insert 120 of the first spacer 100. The first insert 110 is placed on the lip portion including the tumor portion. Thus, if the air communication holes are formed in the first insert 110, the radiation may enter the body through the air communication holes. To the contrary, the second insert 120 is spaced apart from the radiation irradiated area such that the radiation is not irradiated thereto. Thus, the radiation may not be introduced into the body through the air communication holes 121 formed in the second insert 120. Specifically, as shown in FIG. 9, when a lower lip including the tumor portion is disposed on the target support 300, the radiation may be controlled such that the radiation is directed toward the lower lip which is fixed in position by the target support 300 and is not irradiated toward the second insert 120 and an upper lip as a normal portion. Thus, when the air communication holes 121 are formed in the second insert 120, no radiation is applied into the body.

Further, in another embodiment, the radiation is irradiated only toward the first insert placed on the target, and the second insert is constructed to allow the normal portion (e.g., the upper lip in FIG. 9) to be spaced away from the target (e.g., the lower lip in FIG. 9). Thus, when there is no radiation shield inside the oral fixation device, the at least one air communication hole 121 may be easily formed in the second insert 120.

Figure 10:
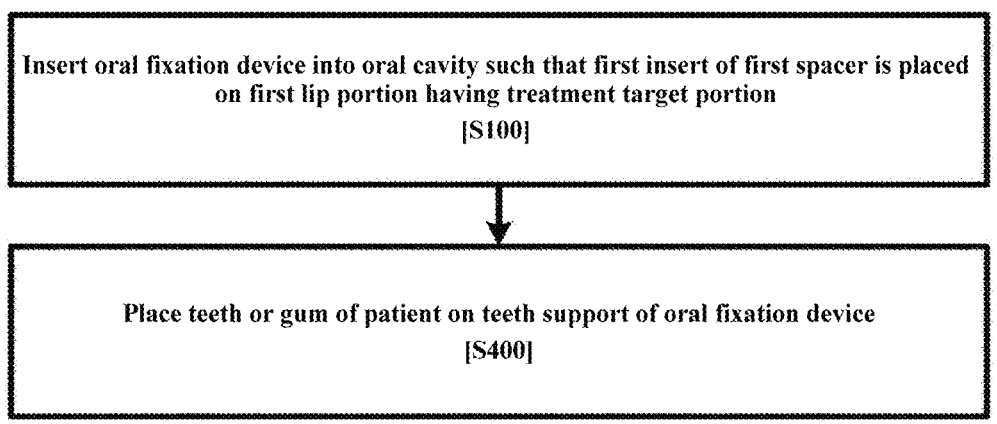
FIG. 10 to FIG. 12 are flowcharts of an oral fixation method for lip cancer treatment according to one embodiment of the inventive concept.
Figure 11:
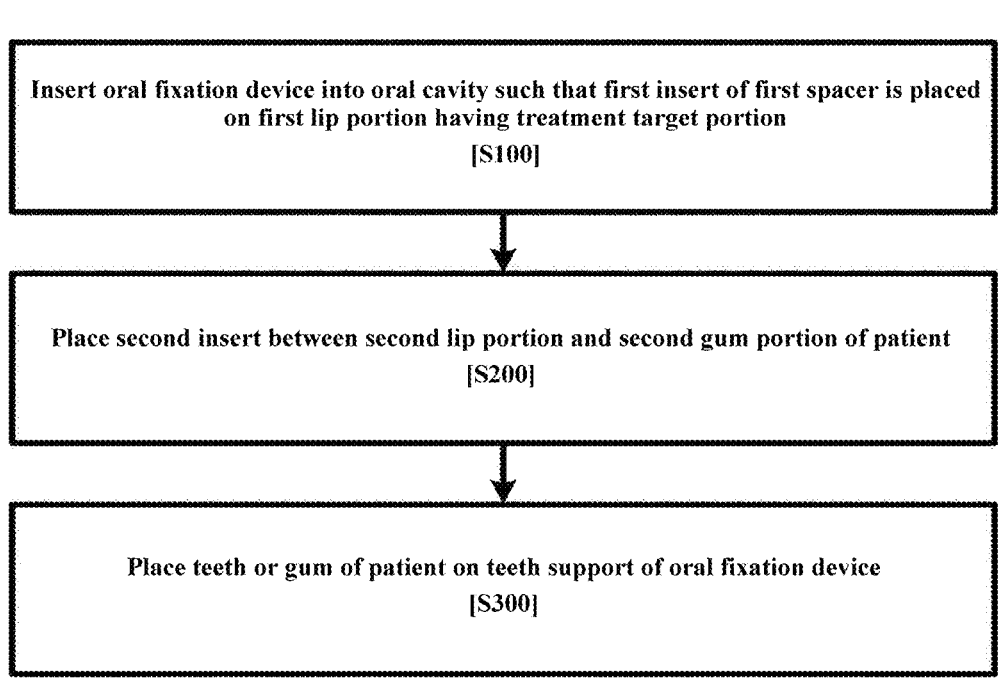
Figure 12:
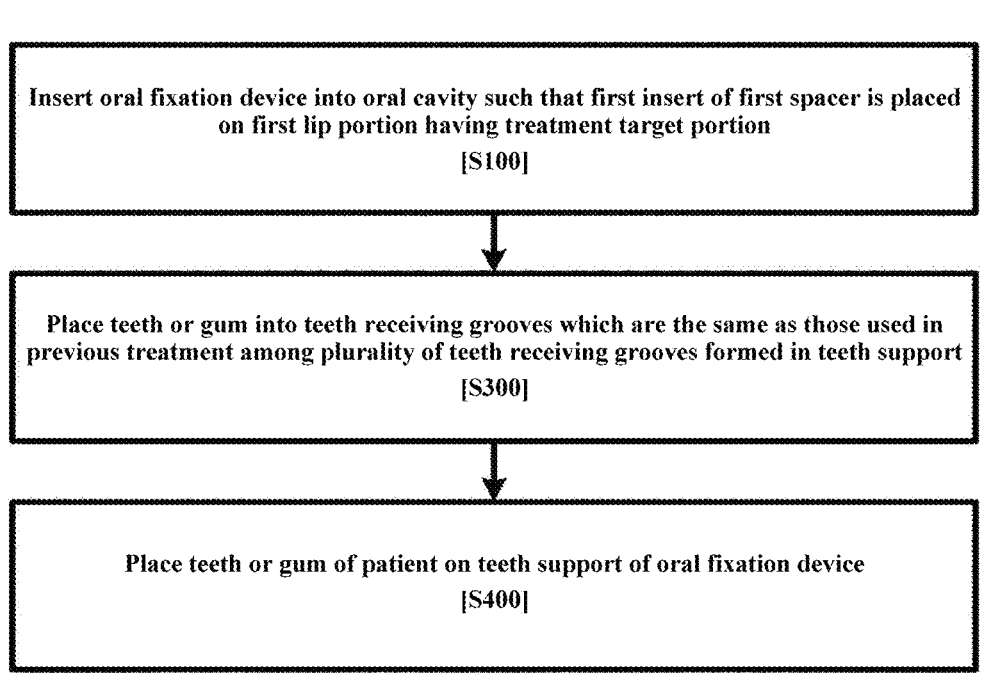

Further, in another embodiment, when the oral fixation device includes the radiation shield in both of the first insert and the second insert, the radiation shield has air communication holes defined therein at the same positions as those defined in the second insert 120. In this connection, in the oral fixation device, the radiation shield may be inserted inside the first spacer, and, then, the at least one air insertion hole 121 may be defined in the second insert 120. FIG. 10 to FIG. 12 are flow charts of an oral fixation method for radiation therapy in a patient with a lip cancer according to another embodiment of the inventive concept.

Referring to FIG. 10, the oral fixation method according to another embodiment of the inventive concept includes inserting the oral fixation device into the oral cavity such that the first insert 110 of the first spacer 100 is disposed on the first lip portion where the treatment target portion is located S100, and supporting the teeth or the gums of the patient on the tooth support 200 of the oral fixation device S400.

The oral fixation device is inserted into the oral cavity such that the first insert 110 of the first spacer 100 is placed on the first lip portion where the treatment target portion is located S100. The oral fixation device may be the device described in the embodiments of the inventive concept. The clinician places the first insert 110 of the first spacer 100 between the first lip portion and the first gum portion such that the first lip portion and the first gum portion are spaced apart from each other by the second spacing corresponding to the thickness of the first insert 110 or the sum of the thickness of the first insert 110 and the height of the target support 300 in the protruding direction.

The tooth support 200 of the oral fixation device supports the patient's teeth or the gum S400. That is, the patient bites the tooth support 200 of the inserted oral fixation device using the teeth or the gum to fix the oral fixation device inside the oral cavity at a state in which the oral fixation device is previously placed in the oral cavity by the medical staff.

In this way, the oral fixation device may maintain the spacing between the first lip portion where the tumor is located and the first gum portion at a spacing at which the radiation may not damage the first gum portion upon radiation irradiation to the first lip portion. Thus, a construction of the oral cavity may be in a state which the radiation therapy may be performed only toward the tumor portion of the first lip portion.

Further, as shown in FIG. 11, when the first spacer 100 of the oral fixation device has the second insert 120, the medical staff inserts the oral fixation device into the oral cavity so that the second insert 120 is positioned between the patient's second lip portion and the second gum portion S200. In this manner, the first lip portion and the second lip portion may be spaced apart from each other by the first spacing so that no radiation is irradiated onto the second lip portion during the radiation therapy toward the first lip portion.

Further, as shown in FIG. 12, when the radiation therapy is performed multiple times toward the same lip cancer tumor of the same patient under the same condition, the patient places the teeth or the gum into the teeth receiving grooves 210 which are the same as those used in a previous treatment among the plurality of teeth receiving grooves 210 formed in the tooth support 200 of the oral fixation device S300. In this way, the same oral cavity construction may be repeatedly reproduced during multiple times of radiation therapy.

According to the inventive concept as described above, following various effects may be achieved.

First, the lip portion in which the tumor is located may be spaced apart from another normal body portion, thereby preventing the normal tissue from being damaged upon irradiation toward the tumor tissue.

Second, the optimal oral fixation device may be selected and used based on a type of the radiation device as used (i.e., the electron beam application device or the photon beam application device). For example, when performing the lip cancer treatment using the photon beam, the photon beam may be irradiated toward the tumor from a side of the lip.

Thus, the oral fixation device may be used to maintain a specific spacing between the lip and the gum so that the photon beam is not irradiated to the normal gum tissue.

Third, when the radiation therapy is performed multiple times, the patient's teeth or gums tip may be placed in the same teeth receiving grooves 210 of the tooth support 200. Thus, the radiation therapy may be repeated by reproducing the same oral cavity fixation state. In this way, the radiation treatment may be simply and repeatedly performed on the same lesion, that is, the tumor location.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An oral fixation device for radiation therapy, the oral fixation device comprising:
   a first spacer comprising:
      a first insert configured to be inserted between a first lip portion and a first gum portion of a mouth of a subject patient; and
      a second insert configured to be disposed between a second lip portion and a second gum portion of the mouth of the subject patient; and
   a tooth support
      coupled to the first spacer at a first surface of the first spacer, which is configured to face an oral cavity of the subject patient, and
      configured to support teeth and/or gums of the subject patient,
   wherein the first spacer has a first thickness and is configured to maintain a first spacing between the first lip portion and the first gum portion,
   wherein the first lip portion includes a treatment target portion to be subjected to the radiation therapy,
   wherein the first insert and the tooth support are connected such that a longitudinal axis of the first insert forms a right angle with a longitudinal axis of the tooth support,
   wherein the second insert and the tooth support are connected such that a longitudinal axis of the second insert forms an acute angle with the longitudinal axis of the tooth support,
   wherein the second insert is inwardly inclined toward the tooth support, with respect to the longitudinal axis of first insert, and
   wherein the second insert has a first height and is configured to maintain at least a second spacing between the first lip portion and the second lip portion.

2. The oral fixation device of claim 1, wherein the oral fixation device further comprises:
   a target support
      protruded from a second surface of the first spacer, and
      configured to be disposed between the first lip portion and the first gum portion to maintain a third spacing between the first lip portion and the first gum portion,
   wherein the target support and the second surface of the first spacer are connected at a right angle.

3. The oral fixation device of claim 2, wherein the target support has a curvature conforming to a shape of a front of the subject patient's mouth when the subject patient's mouth is open.

4. The oral fixation device of claim 1, wherein the oral fixation device further comprises:
   a target support
      protruded from a second surface of the first spacer, and
      configured to hold the treatment target portion in a particular position constantly during multiple exposures in the radiation therapy,
   wherein the target support and the second surface of the first spacer are connected at a right angle.

5. The oral fixation device of claim 1, wherein the oral fixation device further comprises:
   a radiation shield
      positioned inside the first spacer, and
      configured to be positioned between the first lip portion and the first gum portion of the mouth of the subject patient.

6. The oral fixation device of claim 1, wherein the oral fixation device further comprises a handle coupled to the first spacer or the tooth support, wherein the handle configured to extend out of the oral cavity.

7. The oral fixation device of claim 1, wherein the tooth support has a plurality of tooth receiving grooves, which have different distances from a center of the first spacer.

8. The oral fixation device of claim 1, wherein the second insert comprises:
   one or more air communication holes configured to introduce air into the oral cavity to allow the subject patient to breathe when the oral fixation device is fixed within the oral cavity,
   wherein the one or more air communication holes is configured to be positioned between the second lip portion and the second gum portion of the mouth of the subject patient.

9. A method of fixedly positioning the oral fixation device of claim 1 within an oral cavity of the subject patient during treatment of a lip cancer, the method comprising:
   inserting the oral fixation device into the oral cavity such that the first insert of the first spacer is placed on the first lip portion having the treatment target portion; and
   placing the teeth or the gums of the subject patient on the tooth support of the oral fixation device.

* * * * *